(12) United States Patent
Johnson (10) Patent No.: US 7,572,270 B2
(45) Date of Patent: *Aug. 11, 2009

(54) BALLOON CATHETER STENT DELIVERY SYSTEM WITH RIDGES

(75) Inventor: Eric Gerard Johnson, New Albany, IN (US)

(73) Assignee: Cordis Corporation, Miami Lakes, FL (US)

( * ) Notice: Subject to any disclaimer, the term of this patent is extended or adjusted under 35 U.S.C. 154(b) by 610 days.

This patent is subject to a terminal disclaimer.

(21) Appl. No.: 10/466,029

(22) PCT Filed: Feb. 15, 2002

(86) PCT No.: PCT/US02/04636

§ 371 (c)(1), (2), (4) Date: Dec. 24, 2003

(87) PCT Pub. No.: WO02/066096

PCT Pub. Date: Aug. 29, 2002

(65) Prior Publication Data

US 2004/0106973 A1 Jun. 3, 2004

Related U.S. Application Data

(60) Provisional application No. 60/269,430, filed on Feb. 16, 2001.

(51) Int. Cl.
*A61F 2/06* (2006.01)
*A61M 29/00* (2006.01)

(52) U.S. Cl. ...................... 606/194; 623/1.11

(58) Field of Classification Search ............... 606/194, 606/191, 198, 195, 108; 623/1.11, 1.12, 623/1.28
See application file for complete search history.

(56) References Cited

U.S. PATENT DOCUMENTS

| | | | |
|---|---|---|---|
| 4,733,665 A | 3/1988 | Palmaz |
| 4,739,762 A | 4/1988 | Palmaz |
| 4,762,128 A | 8/1988 | Rosenbluth |

(Continued)

FOREIGN PATENT DOCUMENTS

EP    0 335 341 B1    10/1989

(Continued)

OTHER PUBLICATIONS

European Search Report dated Mar. 26, 2007 for corresponding Appln. No. EP 02 71 4922.

(Continued)

*Primary Examiner*—Vy Q. Bui (57) ABSTRACT

A balloon catheter and stent delivery system for medical treatment of a patient includes a balloon having a pattern of ridges in an initial deflated state. The ridges may cooperate with structural elements of a stent crimped onto the balloon, to increase and enhance longitudinal retention of the stent while the catheter system is advanced or withdrawn. Upon inflation, the balloon recovers to an inflated shape having a cylindrical working portion. The balloon catheter thus provides for uniform expansion of the stent when the balloon is inflated. The present invention also tends to protect the leading or distal end of the stent during advancement, and tends to protect the proximal end of the stent during any withdrawal of the catheter system.

18 Claims, 7 Drawing Sheets

U.S. PATENT DOCUMENTS

| | | | |
|---|---|---|---|
| 4,776,337 A | 10/1988 | Palmaz | |
| 4,906,244 A | 3/1990 | Pinchuk et al. | |
| 4,950,227 A | 8/1990 | Savin et al. | |
| 5,104,404 A | 4/1992 | Wolff | |
| 5,108,416 A | 4/1992 | Ryan et al. | |
| 5,242,399 A | 9/1993 | Lau et al. | |
| 5,254,091 A | 10/1993 | Aliahmad et al. | |
| 5,370,615 A | 12/1994 | Johnson | |
| 5,395,390 A | 3/1995 | Simon et al. | |
| 5,403,341 A | 4/1995 | Solar | |
| 5,409,495 A | 4/1995 | Osborn | |
| 5,429,597 A * | 7/1995 | DeMello et al. | 604/509 |
| 5,478,320 A | 12/1995 | Trotta | |
| 5,484,411 A | 1/1996 | Inderbitzen et al. | |
| 5,549,635 A | 8/1996 | Solar | |
| 5,632,760 A | 5/1997 | Sheiban et al. | |
| 5,645,560 A | 7/1997 | Crocker et al. | |
| 5,645,789 A | 7/1997 | Roucher, Jr. | |
| 5,658,311 A | 8/1997 | Baden | |
| 5,672,169 A | 9/1997 | Verbeek | |
| 5,695,498 A | 12/1997 | Tower | |
| 5,746,745 A | 5/1998 | Abele et al. | |
| 5,792,106 A | 8/1998 | Mische | |
| 5,792,172 A | 8/1998 | Fischell et al. | |
| 5,792,415 A | 8/1998 | Hijlkema | |
| 5,810,871 A | 9/1998 | Tuckey et al. | |
| 5,836,965 A | 11/1998 | Jendersee et al. | |
| 5,913,871 A | 6/1999 | Werneth et al. | |
| 5,935,135 A | 8/1999 | Bramfitt et al. | |
| 5,954,740 A * | 9/1999 | Ravenscroft et al. | 606/194 |
| 5,968,069 A | 10/1999 | Dusbabek et al. | |
| 5,971,990 A | 10/1999 | Venturelli | |
| 6,027,510 A * | 2/2000 | Alt | 606/108 |
| 6,056,906 A | 5/2000 | Werneth et al. | |
| 6,063,092 A | 5/2000 | Shin | |
| 6,099,455 A * | 8/2000 | Columbo et al. | 600/3 |
| 6,099,562 A | 8/2000 | Ding et al. | |
| 6,153,252 A * | 11/2000 | Hossainy et al. | 427/2.3 |
| 6,159,229 A | 12/2000 | Jendersee et al. | |
| 6,289,568 B1 | 9/2001 | Miller et al. | |
| 6,293,959 B1 | 9/2001 | Miller et al. | |
| 6,306,162 B1 * | 10/2001 | Patel | 623/1.11 |
| 6,309,402 B1 | 10/2001 | Jendersee et al. | |
| 6,309,411 B1 | 10/2001 | Lashinski et al. | |
| 6,464,718 B1 | 10/2002 | Miller et al. | |

FOREIGN PATENT DOCUMENTS

| | | |
|---|---|---|
| EP | 0 409 929 B1 | 1/1991 |
| EP | 0 442 657 A2 | 8/1991 |
| EP | 0 442 657 A3 | 8/1991 |
| EP | 0 707 837 A1 | 4/1996 |
| EP | 0 714 640 A1 | 6/1996 |
| EP | 0 770 366 B1 | 5/1997 |
| EP | 0 778 010 B1 | 6/1997 |
| EP | 0 778 012 A2 | 6/1997 |
| EP | 0 778 012 A3 | 6/1997 |
| EP | 0 779 062 A1 | 6/1997 |
| EP | 0 850 605 A2 | 7/1998 |
| EP | 0 850 605 A3 | 7/1998 |
| EP | 0 855 171 A2 | 7/1998 |
| EP | 0950386 A2 | 10/1999 |
| WO | WO 95/33422 | 12/1995 |
| WO | WO 97/21400 | 6/1997 |
| WO | WO 01/00109 A1 | 1/2001 |

OTHER PUBLICATIONS

Supplementary European Search Report EP 02718995 dated Mar. 20, 2007.

* cited by examiner

BALLOON CATHETER STENT DELIVERY SYSTEM WITH RIDGES

CROSS-REFERENCE TO RELATED APPLICATION

This application claims priority of United States Provisional Patent Application No. 60/269,430 filed Feb. 16, 2001.

BACKGROUND AND SUMMARY OF INVENTION

1. Technical Background

The present invention relates generally to medical devices, and more particularly to a balloon catheter and stent delivery system.

2. Discussion

The present invention involves a balloon catheter for inserting a stent, vascular scaffold, or other medical device to a desired site in a patient for medical treatment The balloon is specially shaped with structural features for cooperating with corresponding stent designs to enhance stent retention.

For purposes of brevity, the following background and description will focus generally on the example of a medical device delivery system, in which the medical device is a stent, and the delivery system is based on a balloon catheter. Of course, other medical devices and other delivery systems that are within the scope of one of the claims below are included in the present invention.

It is desirable to provide a novel combination stent delivery system, along with a unique manufacturing process, having an optimum arrangement of several features. These desirable features include a tendency to retain the stent in position on a deflated balloon, small initial size or profile, bending flexibility, column stiffness or pushability, pull strength, inflation strength (sometimes referred to as "rated burst pressure"), etc.

To provide an optimum arrangement of these features, the present invention recognizes and takes advantage of structural aspects of certain stents, such that the delivery system optimizes stent retention without compromising any of the other performance qualities.

Among the stent structural features that may be utilized by the present invention are an expandable cylindrical mesh or lattice, stents are preferably designed to be flexible during delivery and bend along a vascular path. One design that allows such flexibility is to include a series of main elements for hoop strength, preferably coupled by a series of flexible links to enhance flexibility. The stent should preferably also have an optimum selection of features, including flexibility, small profile, hoop strength when expanded, and resilience, etc.

Accordingly, stent delivery systems of the present invention provide balloons for delivery and expanding the stent, in which the balloon has a deflated shape with a pattern of ridges or bumps. These ridges or bumps tend to increase stent retention during delivery, and preferably cooperate with the pattern of main stent elements and flexible links, to better hold the stent in place on the catheter delivery system.

BACKGROUND

Balloon catheters are used in a variety of therapeutic applications, including intravascular catheters for procedures such as angioplasty treating coronary, neurological and peripheral blood vessels partially or totally blocked or narrowed by a stenosis. By way of example, the present invention will be described in relation to coronary and peripheral angioplasty treatments. However, it should be understood that the present invention relates to balloon catheters and stent delivery systems generally, and is not limited to the specific embodiments described herein.

Most balloon catheters have a relatively long and flexible tubular shaft defining one or more passages or lumens, and an inflatable balloon attached near one end of the shaft. This end of the catheter where the balloon is located is customarily referred to as the "distal" end, while the other end is called the "proximal" end. The balloon is connected to one of the lumens extending through the shaft to selectively inflate and deflate the balloon. The other end of this inflation lumen leads to a hub coupling at the other end for connecting the shaft lumens to various equipment. Examples of this type of balloon catheter are shown in U.S. Pat. No. 5,304,197, entitled "Balloons For Medical Devices And Fabrication Thereof," issued to Pinchuk et al. on Apr. 19, 1994, and also in U.S. Pat. No. 5,370,615, entitled "Balloon Catheter For Angioplasty," issued to Johnson on Dec. 6, 1994.

A common treatment method for using such a balloon catheter is to advance the catheter into the body of a patient, by directing the catheter distal end percutaneously through an incision and along a body passage until the balloon is located within the desired site. The term "desired site" refers to the location in the patient's body currently selected for treatment by a health care professional. A larger guiding catheter may often be used to access the local area near the desired site, providing a smooth, supported lumen for conducting other devices including balloon catheters to the desired site. After the balloon is within the desired site, it can be selectively inflated to press outward on the body passage at relatively high pressure to a relatively constant diameter, in the case of an inelastic or non-compliant balloon material.

This outward pressing of a constriction or narrowing at the desired site in a body passage is intended to re-open or dilate that body passageway or lumen, increasing its inner diameter or cross-sectional area. When performed in a blood vessel, this procedure is called "angioplasty." The narrowing of the body passageway lumen is called a lesion or stenosis, and may be formed of hard plaque or viscous thrombus. The objective of this angioplasty procedure is to treat the lesion by increasing the cross-sectional area of the blood vessel, to encourage greater blood flow through the newly expanded vessel.

Unfortunately, the lumen at the angioplasty site may re-close or become narrow again. This possible phenomenon is called restenosis, and may occur in a certain percentage of percutaneous transluminal angioplasty patients. Restenosis may require an additional procedure, such as another angioplasty, drug therapy treatment, or even surgery including bypass graft.

Stents:

In an effort to prevent restenosis, a short flexible cylinder or scaffold made of metal or polymers, referred to as a stent, may be permanently implanted into the vessel to hold the lumen open, to reinforce the vessel wall and improve blood flow. In 1998, coronary stents were placed in an estimated half million patients in the United States. The presence of a stent tends to successfully keep the blood vessel open longer, but their use may be limited by various factors, including size and location of the blood vessel, a complicated or tortuous vessel pathway, etc. Also, even a vessel with a stent may eventually develop restenosis.

One type of stent is expanded to the proper size at the desired site within the lesion by inflating a balloon catheter, referred to as "balloon-expandable" stents. Balloon-expandable stents are crimped or compressed onto a deflated balloon, to a diameter during delivery that is smaller than the eventual deployed diameter at the desired site.

However, friction forces during delivery may tend to cause a crimped stent to slip in a proximal direction while the catheter system is advanced, or possibly to slip in a distal direction if the physician decides to withdraw the stent without deploying it. It is of course desirable to retain the stent in the proper position during movement, both advancement along a vascular path to the desired site, as well as, subsequent removal if necessary.

In addition, it is desirable to provide a stent delivery system with greater stent retention, that is more capable of holding the stent in position, or also of advancing a crimped stent across a previously deployed stent, or possibly withdrawing it into a guiding catheter.

Drug Delivery:

The present invention is preferably used with a stent or other medical device that may be provided with one or more coatings, to achieve even greater effectiveness. Such coating or coatings may be selected among various coatings, including therapeutic coatings such as anticoagulants, antiproliferatives, or antirestenosis compounds.

For example, a preferred coating for a stent is an anticoagulant coating such as heparin. Another preferred coating is an antirestenosis compound, such as for example rapamycin (which is also known as sirolimus). Such a compound can be very effective at resisting a vessel from re-closing. Any particular coating or type of coating may of course be used independently or in conjunction with any one or more coatings, as desired.

Some pioneering research in drug-coated stents has been conducted, and is described in the following publications, all of which are assigned to Cordis Corporation and are incorporated herein by reference: (i) European Patent Application number EP 99/302918 A2, entitled "Stent With Local Rapamycin Delivery" by Wright et al., filed on Apr. 15, 1999, (ii) PCT Patent Application number US0115562, entitled "Delivery Devices For Treatment Of Vascular Disease" by Falotico et al., filed on May 14, 2001; and (iii) PCT Patent Application number US0115564, entitled "Drug/Drug Delivery Systems For The Prevention And Treatment Of Vascular Disease" by Falotico et al., filed on Oct. 14, 2001.

Accordingly, it is an object of the present invention to provide balloon catheter systems for enhanced position retention of a stent or other medical device during longitudinal movement of the catheter.

It is a further object of the present invention to provide methods for making balloon catheter systems having enhanced position retention of a stent or other medical device.

It is a further object of the present invention to provide methods for making balloon catheters for enhanced stent position retention.

These and various other objects, advantages and features of the invention will become apparent from the following description and claims, when considered in conjunction with the appended drawings.

DETAILED DESCRIPTION OF THE PREFERRED EMBODIMENT

The following description of the preferred embodiments of the present invention is merely illustrative in nature, and as such it does not limit in any way the present invention, its application, or uses. Numerous modifications may be made by those skilled in the art without departing from the true spirit and scope of the invention.

The present invention relates to a medical device delivery system having a balloon that is specially shaped when deflated with a series of ridges or bumps, for cooperating with corresponding designs of the medical device to enhance position retention of the medical device during movement of the system. The present invention may preferably be used with a medical device having one or more coatings, such as a therapeutic drug coating.

Balloon Catheters:

Referring to the drawings, a balloon catheter system is depicted, with one of the preferred embodiments of the present invention being shown generally at 10. The balloon catheter of FIG. 1 has an inflatable balloon 12, a relatively long and flexible tubular shaft 14, and a hub 16. The balloon 12 is affixed to the shaft 14 near a distal end of the shaft 14, and the hub 16 is affixed to the proximal end of the shaft 14.

Figure 1:
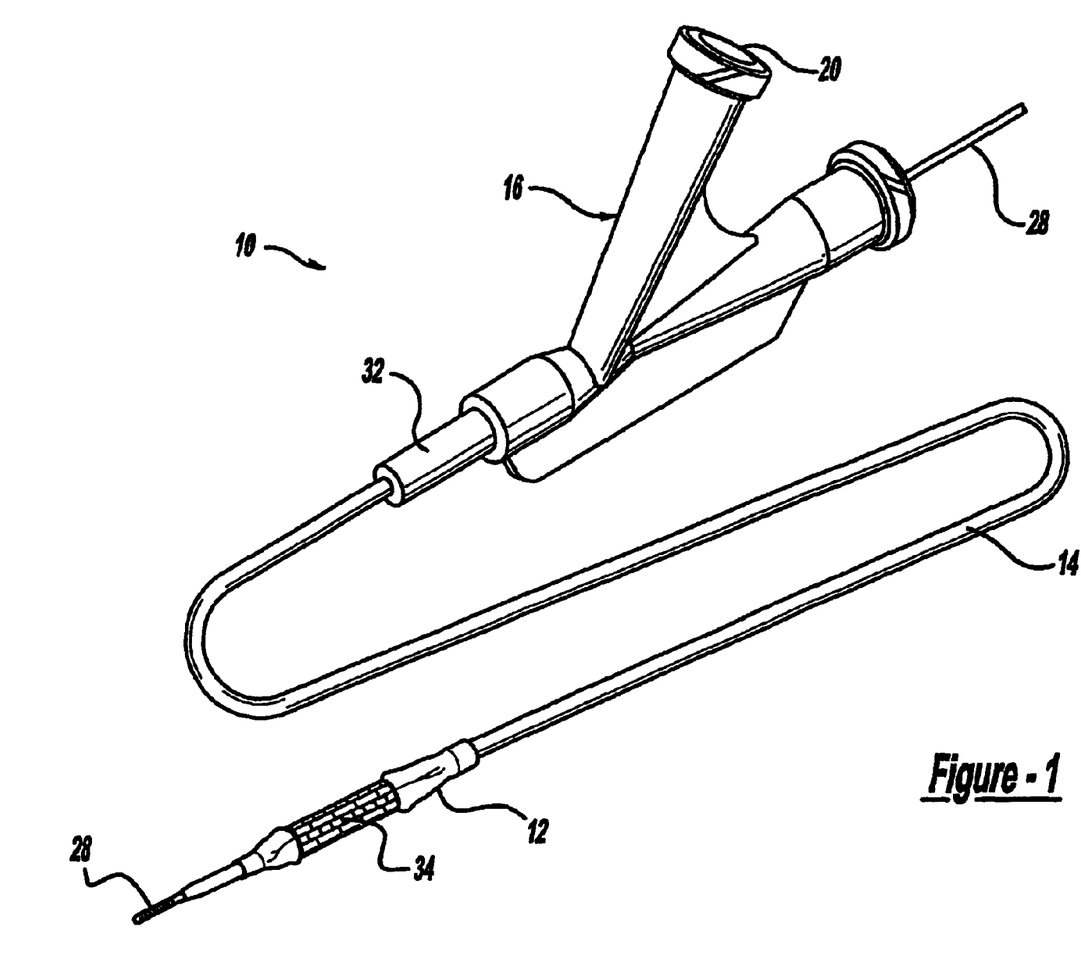
FIG. 1 is an external perspective view of a balloon catheter having a stent mounted around the balloon, arranged according to the principles of the present invention.

The shaft 14 defines one or more passages or lumens extending through the shaft, at least one of which is an inflation lumen 18 connected to the balloon 12 for the purpose of selectively inflating and deflating the balloon 12. The inflation lumen 18 thus provides fluid communication between the interior of the balloon 12 at the distal end of the inflation lumen 18, and a hub inflation port 20 having a coupling or luer-lock fitting at the proximal end for connecting the inflation lumen 18 to a source of pressurized inflation fluid (not shown) in the conventional manner.

Figure 2:
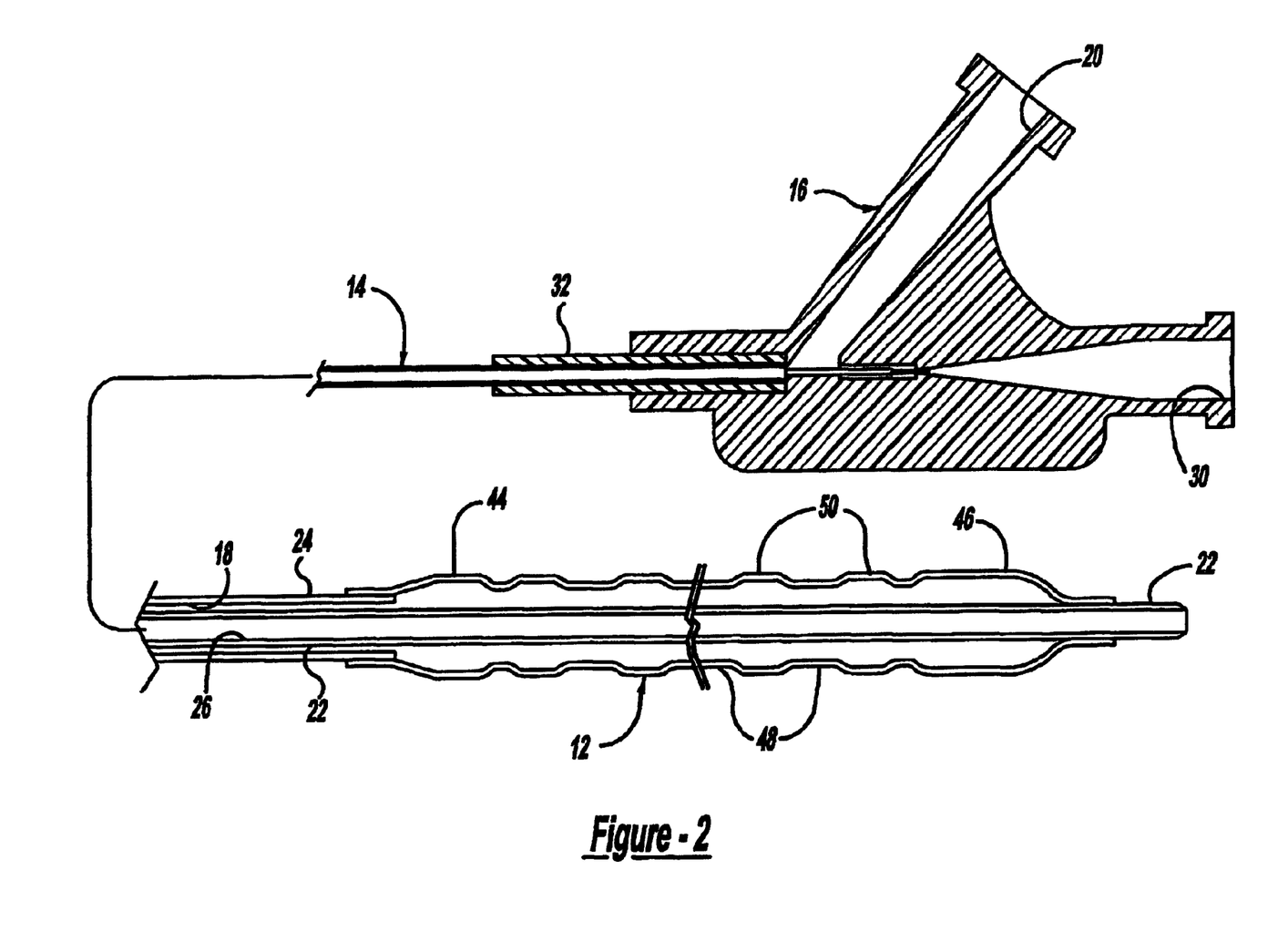
FIG. 2 is a longitudinal cross-section view of a balloon catheter according to the principles of the present invention.

In the illustrated embodiment, the shaft 14 is constructed of an inner and outer tubular body 22 and 24. The inner body 22 defines a guidewire lumen 26, while the inflation lumen 18 is defined by the annular space between the inner and outer tubular bodies 22 and 24. The guidewire lumen 26 is adapted to receive an elongated flexible guidewire 28 in a sliding fashion, such that the guidewire 28 and catheter 10 may be advanced or withdrawn independently, or the catheter 10 may be guided along a path selected with the guidewire 28. The shaft 14 may of course have various configurations instead of this coaxial design, including a single extruded tube defining any suitable number of parallel side-by-side lumens, or a proximal shaft portion formed of a metal hypotube connected to a polymer distal shaft portion or other designs. Moreover, the catheter shaft may have a rapid exchange configuration, in which the guidewire exits the shaft at a proximal guidewire port located between the balloon and the hub.

The proximal hub 16 is affixed to the proximal end of the shaft 14, and preferably provides an inflation port 20 and a guidewire port 30, again with a luer-lock fitting or hemostatic valve (not shown). Such a valve allows the guidewire 28 to traverse and slide within the guidewire lumen 26, yet while resisting the loss of blood or other fluids through the guidewire lumen 26 and guidewire port 30.

As shown in the drawings, the inner and outer tubular bodies 22 and 24 are securely received within the hub 16, and surrounded by a tubular strain relief 32. The hub 16 provides fluid communication between the guidewire lumen 26 and a guidewire port 30 as well as between the annular inflation lumen 18 and the inflation port 20 and coupling.

Figure 5:
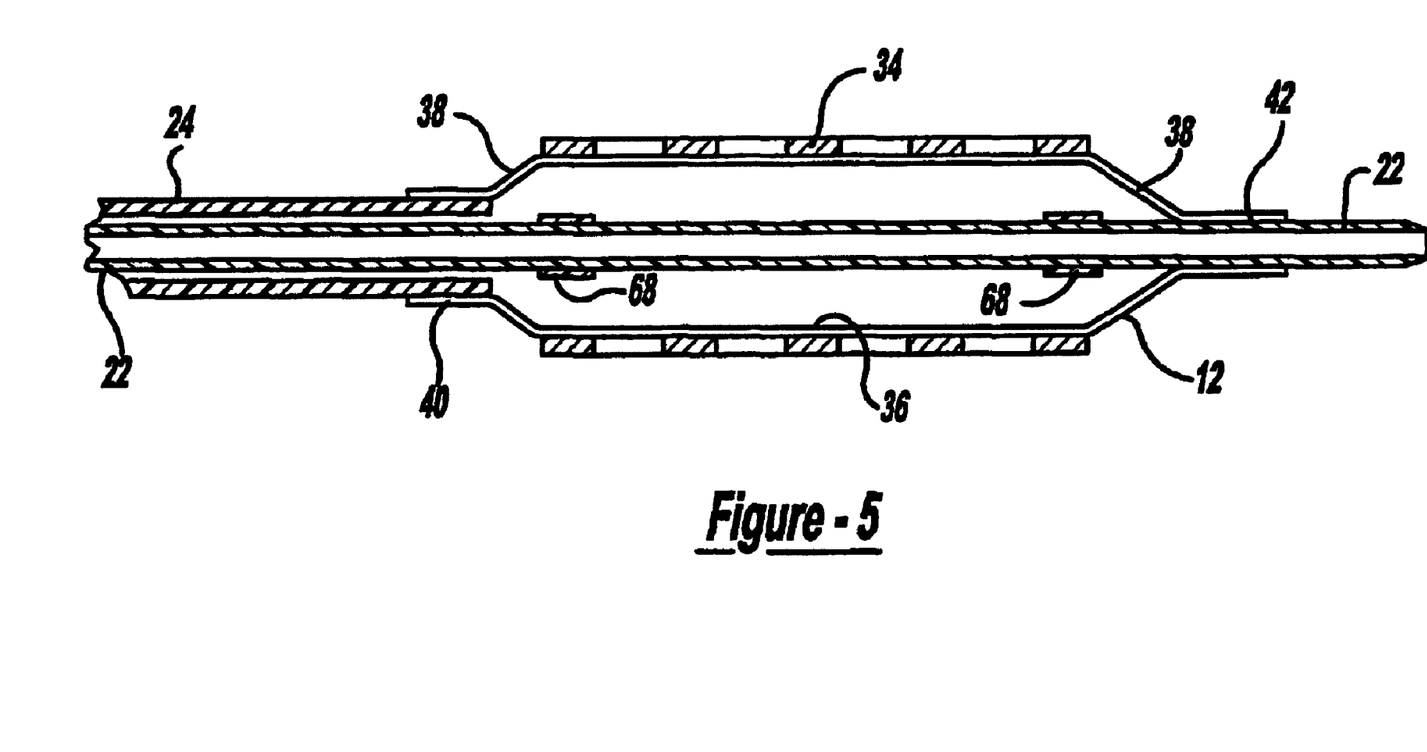
FIG. 5 is a partial longitudinal cross-section view of a stent and a balloon catheter, showing a fully inflated balloon.
Figure 6:
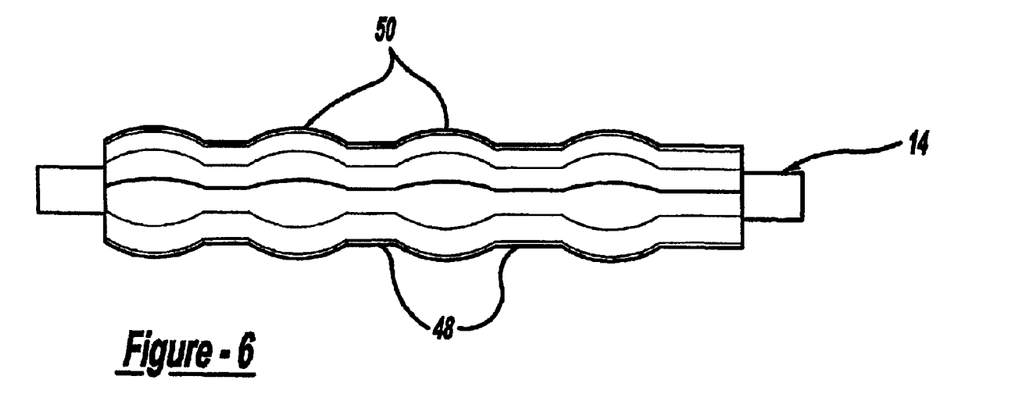
FIGS. 6-8 are partial elevation views of a balloon catheter distal end and a stent.
Figure 7:
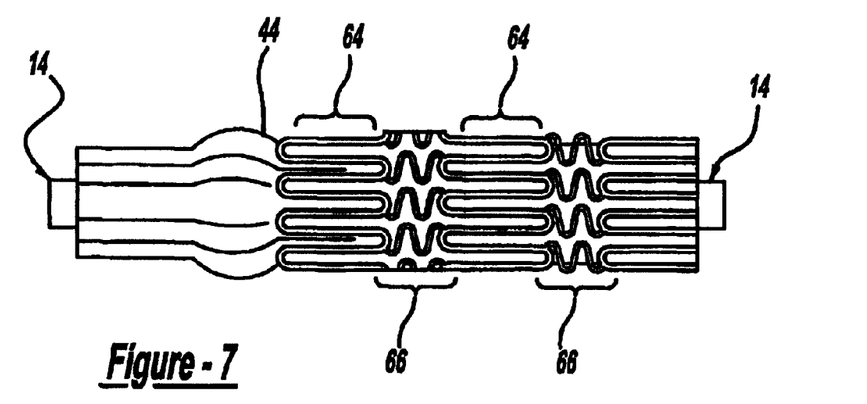
Figure 8:
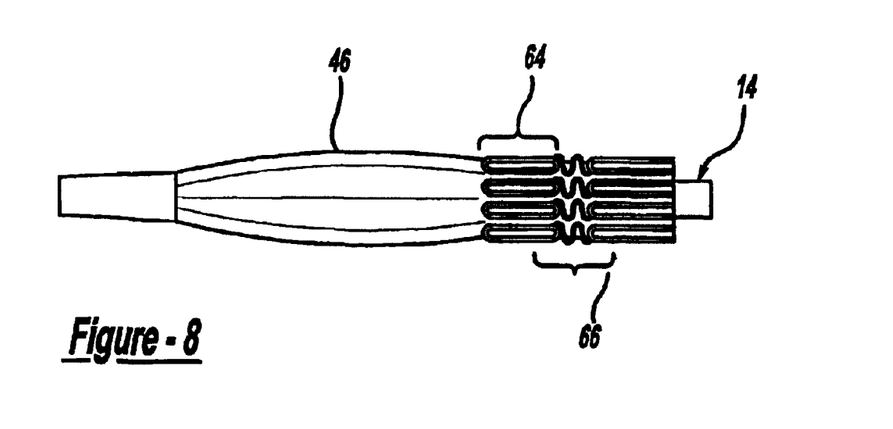

As shown in the drawings, in particular FIG. 5, the balloon 12 in its fully inflated profile shape has a cylindrical working portion 36 with an inflated diameter located between a pair of conical end portions 38, and a pair of proximal and distal legs 40 and 42 affixed to the shaft 14. In its deflated shape, the balloon 12 preferably has several pleats that are wrapped around the shaft. The balloon pleats are illustrated in FIGS. 1 and 6-8 in diagrammatic fashion, but are omitted from the other drawings for the sake of clarity.

Radiopaque markers may be used to indicate the position(s) of certain components or features on an x-ray video fluoroscope. For example, marker bands 68 may be attached to the inner body 22 as shown in FIG. 5, to indicate the positions of the proximal and distal ends of a stent 34.

Various materials for balloon catheter components are well known. For example, the balloon material is preferably substantially inelastic, and as such it stretches a relatively small amount under pressures of up to 15 atmospheres or more. Different balloon materials may be used, including nylon, PEEK, polymer materials sold under the trade name Pebax or Plexar, polyethylene, HDPE, polyurethane, or a block copolymer thereof. Likewise, various materials may be used for the shaft components and strain relief, including for example all of the materials listed above, as well as others including metal such as a stainless steel hypotube for example. The hub may be made of a hard plastic, such as for example polycarbonate. Markers 68 may be made of any suitably radiopaque material, metal, alloy, or combination of materials, including for example tungsten or platinum.

Also, various material structures may be used for any of the components, including for example multilayer structures such as two layers with different properties, or reinforced or braided structures.

Stents and Other Medical Devices:

A stent of any suitable type or configuration may be provided with a catheter 10 of the present invention. Preferably, stents for the present invention should have an optimum selection of various features, including among others: a generally cylindrical shape, small initial diameter, large deployed diameter, flexibility, high hoop strength when deployed, closed cell construction, and certain other desirable performance characteristics common to balloon-expandable stents. Any stent design having the desired characteristics may be used with the present invention.

Various kinds and types of stents are available in the market, and some different currently available stents are acceptable for use in the present invention, as well as new stents which may be developed in the future. The stent 34 depicted in the drawings is a cylindrical metal mesh stent having an initial crimped outer diameter, which may be forcibly expanded by the balloon to a deployed diameter. When deployed in a body passageway of a patient, the stent may be designed to preferably press radially outward to hold the passageway open.

An example of a stent with a preferred combination of features is known as the Bx Velocity, available from Cordis Corporation in Miami, Fla. The Bx Velocity stent has an advantageous arrangement illustrated in FIG. 3, including an alternating series of structural elements for strength and flexible link for flexibility. Of course, the present invention may be used with any stent having a suitable configuration.

Figure 3:
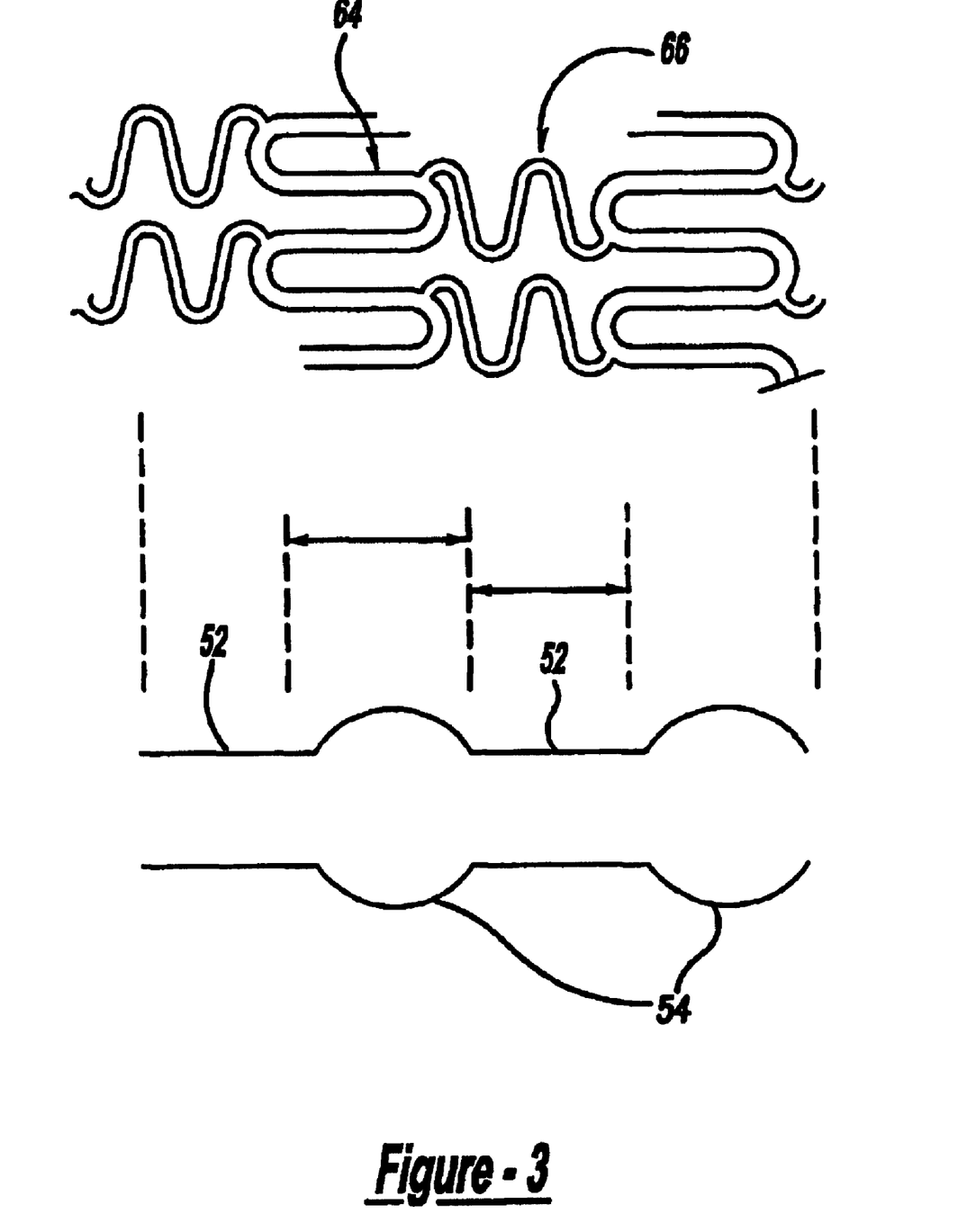
FIG. 3 is a partial cross-section view of a balloon and a corresponding partial pattern view of a section of a stent.

Among the stent structural features that may be included in such a suitable configuration are an expandable cylindrical mesh or lattice, designed to be flexible and bend along a vascular path. An example of a possible design having these features may include a series of main structural elements 64 for hoop strength, coupled by a series of flexible links 66 to enhance flexibility.

The present invention may be used with any other medical device having the requisite features, and which is delivered by a catheter delivery system with the claimed elements.

Preferably, the stent or other medical device may be provided with one or more coatings. Such coating or coatings may be selected among various coatings, including therapeutic coatings such as anticoagulants, antiproliferatives, or anti-restenosis compounds.

For example, a preferred coating for a stent is an anticoagulant coating such as heparin. Another preferred coating is an anti-restenosis compound, such as for example rapamycin (which is also known as sirolimus). Such a compound can be very effective at resisting a vessel from re-closing. Any particular coating or type of coating may of course be used independently or in conjunction with any one or more coatings, as desired.

Because the stent is most often or most likely to be made of metal, for example stainless steel or nitinol, it is preferable that a coating be applied with or used in conjunction with one or more polymers. For example, an initial polymer coating may preferably be applied to the stent. The therapeutic compound may be applied directly or may be embedded in another polymer coating, as desired.

The balloon catheter may be used for inserting a stent, vascular scaffold or other medical device to a desired site in a patient for medical treatment, in which the balloon is specially shaped with structural features for cooperating with corresponding designs of the medical device to enhance position retention.

An optimum combination of features for the device and delivery system include a small initial size or profile, bending flexibility, column stiffness or pushability, pull strength, inflation strength (sometimes referred to as "burst pressure"), and a tendency to retain the stent in position on a deflated balloon.

To provide an optimum arrangement of these features, the present invention recognizes and takes advantage of structural aspects of certain stents, such that the delivery system optimizes stent retention while maintaining the performance qualities.

Ridges or Bumps:

Accordingly, medical device delivery systems of the present invention provide balloons with a deflated shape having a pattern of radially extending ridges 50. These ridges 50 preferably cooperate with the pattern of main structural elements and flexible links, to hold the stent in place on the catheter delivery system.

A novel balloon catheter system of the present invention provides several advantages. Among these advantages is that the balloon in an initial deflated state has a series of ridges or bumps for cooperating with the structure of the selected stent, to enhance stent position retention. This improved stent retention results from crimping a stent around a previously formed balloon having the ridges of the present invention. After crimping, the circumferential ridges formed on the balloon increase stent retention of the delivery system. In the currently preferred embodiment as shown in FIG. 3, the ridges 54 and valleys 52 of the deflated balloon 12 are preferably aligned with a corresponding series of structural stent elements.

Such alignment of the balloon ridges and the stent structural elements preferably involves sizing and positioning each ridge within and surrounded by a corresponding generally cylindrical stent structural element. In other words, as illustrated in FIG. 3, each structural element portion of the stent pattern is preferably arranged to match and be crimped around a corresponding ridge formed on the balloon. The remaining portions of the stent pattern between structural elements, preferably flexible linkages of some kind, should match and be crimped around the remaining portions of the balloon between ridges.

Of course, the inverse arrangement is also within the scope of the present invention in which the structural elements of the stent are aligned between, rather than aligned with, the balloon ridges.

In general, the present invention relates preferably to a stent having a repeating serial pattern, aligned and arranged with a corresponding repeating pattern of shaped features or ridges formed on a deflated, pleated and wrapped balloon on a catheter.

Figure 4A:
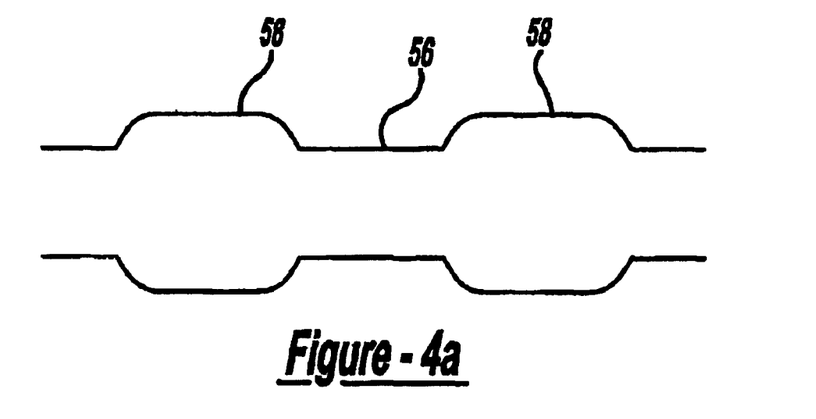
FIG. 4 is a series of partial longitudinal cross-section views of balloons according to alternate embodiments of the present invention.
Figure 4B:
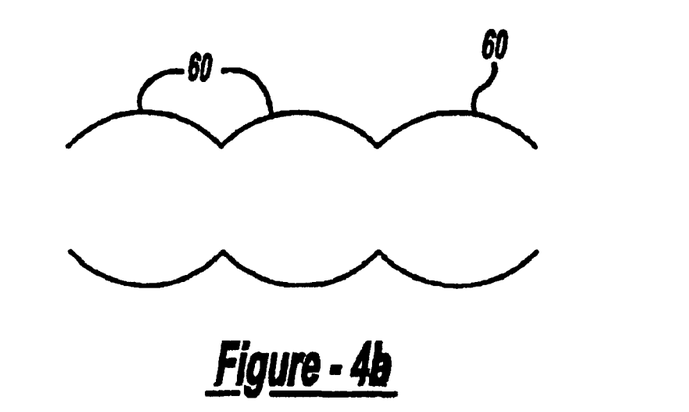

The balloon pattern of shaped features or ridges may also have various shapes, examples of which are shown in FIGS. 4*a*-*c*. The size and shape of the balloon ridges or bumps may be varied to suit preferences, or to optimally accommodate various designs of the stent or of the medical device. FIG. 4*a* for example shows a balloon having valleys 56 and elliptical ridges 58. FIG. 4*b* shows a balloon having adjacent rounded lobes 60. FIG. 4*c* shows a balloon having an undulating or sinusoidal series of shapes 62.

In addition, the balloon preferably defines a pair of shoulders 44 and 46 in the initial deflated shape, proximal and distal of the stent, to further enhance the tendency of the stent to maintain position on the balloon, as well as providing a smooth and gentle surface during advancement and possible retraction of the stent into position. This coordinated design of the balloon and stent optimizes many of the desired performance features of the stent delivery system in general, and increases stent retention in particular.

These preferably curved annular shoulders immediately adjacent the proximal and distal ends of the stent should have a diameter equal to or greater than the crimped stent, thus protecting the stent and minimizing any possibility of the stent moving due to friction. The shoulders and transition portions may also tend to act as dilators, to encourage easy advancement through challenging anatomy or a previously deployed stent, or withdrawal into the guiding catheter. The proximal and distal shoulders may be of any desirable shape, with preferably an outer dimension greater than the crimped stent.

Accordingly, the balloon also has a composite profile shape which varies at different pressures. The balloon initially is in a deflated state and has a deflated profile shape, as specifically illustrated in FIG. 2, having a central bed portion with a deflated bed diameter being flanked by a pair of proximal and distal shoulders 44 and 46 defining deflated shoulder diameters that are preferably larger than the deflated bed diameter.

The balloon shoulders taper smoothly down to proximal and distal cylindrical balloon leg 40 and 42. The proximal balloon leg 40 is affixed to the outer tube 24, while the distal balloon leg 42 is affixed to the inner tube 22. This deflated balloon profile shape thus provides a bed or nest portion for receiving the stent 34 and tending to hold the stent 34 in place, while minimizing friction or adverse contact between the ends of the stent 34 and a blood vessel wall. The present invention thus tends to protect the leading or distal ends of the stent 34 during advancement into the patient's body, and the proximal end of the stent 34 during any withdrawal of the catheter system.

FIG. 5 depicts the balloon 12 in its fully inflated profile shape. The shoulders and ridge shapes disappear, and the balloon profile shape changes or morphs into a different profile shape when inflated at fill inflation pressure. This fully inflated shape provides the preferable cylindrical working portion 36, wherein the portion of the balloon supporting and expanding the stent 34 has an inflated diameter larger than any other portion of the balloon 12. This feature tends to prevent any part of the balloon from expanding excessively, which might cause local trauma to the blood vessel wall.

In the deflated shape, the balloon is therefore temporarily reformed into a different shape than what might conventionally result from simply deflating and pleating a previously known balloon. This temporarily reformed shape enhances stent position retention, and yet exhibits the preferable fully inflated shape.

Many modifications can of course be made to the present invention, and many alternate embodiments of the present invention are possible. Some examples include forming discrete bumps or any other shapes of protrusion, rather than circumferential ridges. Likewise, the ridges or bumps may extend radially outward to differing distances, for example an arrangement of major and minor features. Bumps or features on the same balloon may have different shapes as well as sizes. It is possible that balloon bumps or ridges may extend through or among interstices or gaps in the stent, or have an outer dimension greater than and extending beyond the outer diameter of the stent.

Another advantage of the present invention is the absence of any type of physical collar or other retaining device within the balloon, or on the outer balloon surface, or mounted on the balloon catheter shaft, which might undesirably increase the primary and/or secondary profiles of the stent delivery system.

The dimensions that may be preferred for the present invention will of course vary, as the device is sized to a patient's vascular anatomy. The following dimensions are for example only, and will vary greatly depending on the patient's anatomy; desired area such as coronary vascular, endovascular, or esophageal areas. Accordingly, all of the following dimensions are in inches, and represent only an approximate average of a preferred range of 100%.

The outer diameters of the inner body may be 0.025, of a proximal or distal shoulder may be 0.040-0.060, of the base stent bed may be 0.030-0.050, and of the bumps or ridges may be 0.035-0.065. The longitudinal length of the proximal or distal shoulder may be 0.250, of the bumps or ridges may be 0.030-0.045, and of the gap or distance between bumps or ridges may be 0.040-0.060.

Of course, the ridges may be made by any suitable method, and may have any suitable shape and arrangement, in accordance with the scope of the present invention. The present invention may be made for example using any of the following methods, as well as various modifications that will be apparent to those skilled in the art.

First, a balloon catheter is assembled using generally conventional methods of extrusion, injection molding, and adhesive or heat-sealing for example. Then the balloon is preferably pleated, in which the balloon is folded into any suitable or preferable number of longitudinal pleats. The pleated balloon is preferably heated slightly for a short time, to cause the balloon material to accept a "memory" or a preference for a pleated configuration when deflated. Of course, the pleating step may be conducted in a conventional manner, but the "heat-pleating" step is preferred. For example, if nylon balloon material is used, the heat-pleating may be performed with a temperature of up to approximately 70° C. for up to about half a minute.

The pleated "wings" are then wrapped around a portion of the catheter shaft all in the same direction, either manually or by using a pleating machine.

The balloon is then temporarily held in its pleated condition by slipping a forming tube in the proximal direction onto the pleated balloon, while the assembly is transported to the next processing station. The balloon is heated, preferably at 60-80° C. for under 30 seconds.

Figure 9:
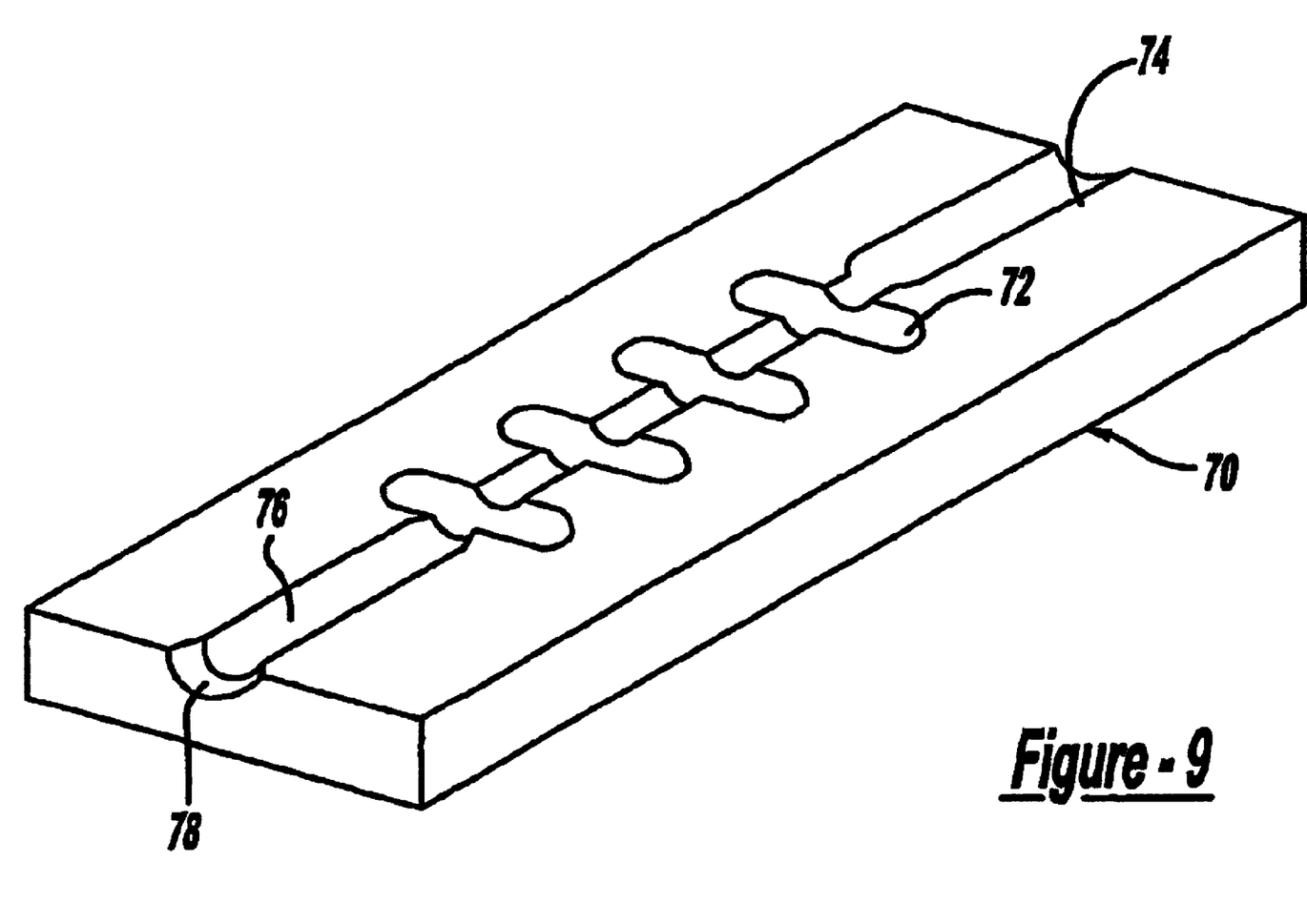
FIG. 9 is a perspective view of an example of balloon forming equipment according to the present invention.

The forming tube may then be removed. The folded and pleated balloon is then placed in a mold 70 to form the desired balloon bumps or ridges. A mold component is shown in FIG. 9, with one possible configuration according to the present invention. The mold 70 is used with an identical and opposing mold, both of which have a series of recesses 72 for creating the desired bumps or ridges. A passage is formed through the mold 70, to allow the catheter to be inserted within the mold 70. This passage has proximal and distal extensions 76 and 74, and the passage extends fully through the length of the mold 70. The proximal end of the proximal extension 76 is chamfered, beveled, or angled 78, to allow easy introduction of the balloon into the mold 70. When the balloon is inside the clamped mold 70, it is pressurized and heated for a time. The mold 70 may be made of any suitably heat-resistant and rigid material, including a transparent material such as acrylic. The heat and pressure may preferably be about 80-100° C. and 175-225 psi for about half a minute. The mold 70, which is preferably a pair of "clam-shell" dies having specific shapes formed in their surfaces, are preferably made of polycarbonate and acrylic inserts, inside a heat-sealing machine. The mold 70 preferably has a desired series of cylindrical and/or doughnut-shaped cut-outs or recesses 72 formed on the interior surface of the mold 70, as illustrated in FIG. 9.

After the pressure is released, the pair of dies which form the mold 70 are opened. The resulting balloon catheter assembly thus exhibits the desirable ridges of the present invention.

A stent is placed over the shaped balloon, such that the stent preferably has structural elements that align with the balloon ridges. The alignment of the stent in position can be facilitated by one or more marker bands on the balloon catheter shaft. The resulting assembly may be placed in a crimping device, which uniformly squeezes the stent onto the balloon. The stent is then gently crimped or compressed around the balloon, with the pleats, ridges and shoulders intact, to a crimped condition in which the stent has a specific crimped outer diameter.

When the balloon is pressurized, a pressurized fluid is applied to the inflation port and through the inflation lumen. The pressure of the inflation within the mold may slightly exceed the rated burst pressure of the balloon, and the mold will prevent expansion of the balloon while allowing the series of ridges or bumps, and proximal and distal balloon shoulders to form. The pressurized fluid may preferably be dry nitrogen, and the pressure may preferably be maintained for a preselected period of time.

The mold used during the process described above may be formed as shown in FIG. 9. While the mold with the accompanying balloon catheter is held under pressure, they are then held in a hot box or heated die. The heat tends to set the balloon in place, thus forming the desired series of ridges or bumps, and proximal and distal shoulders 44 and 46. Of course, a hot air or liquid system may also be used. The preferred temperature of the heating system is preferably below the permanent deformation temperature of the balloon material, and the time and pressure of this process may be extended to ensure that such a temperature will result in the desired composite shape and temporary reformation of the balloon.

The pressure is released and the baloon assembly is then removed from the mold and heating system. In the alternative, the system is no longer heated, but the pressure may be maintained as the balloon assembly is allowed to cool for a period of time. The pressure is released, then the mold is opened.

Several features of this preferred method of making the balloon catheter stent delivery system of the present invention have an effect on the performance of the resulting product, including the temperatures, pressures, time periods, crimped outer diameter of the stent, the internal diameter of the mold, as well as the thermal characteristics of the balloon and mold. These characteristics may be optimized and selected to result in a desired combination of performance attributes for the end product.

It should be understood that an unlimited number of configurations for the present invention could be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

What is claimed is:

1. A balloon catheter stent deployment system, comprising:

a balloon catheter with a flexible shaft having proximal and distal ends, a hub affixed to the shaft proximal end having an inflation port, and an inflatable balloon affixed to the shaft near the shaft distal end; the shaft defining an inflation lumen providing fluid communication of an inflation fluid between the hub inflation port and the balloon;

such that the balloon is adapted for selective inflation from a deflated state to an inflated state, as well as later deflation; the balloon in the inflated state having a cylindrical working portion located between a pair of conical portions and a pair of leg portions affixed to the shaft; the balloon being initially in the deflated state having multiple longitudinal pleats wrapped around a portion of the shaft;

an expandable tubular mesh stent defining a tubular wall thickness, mounted around the balloon and being crimped in an initial state to an initial crimped outer diameter; the stent in the initial state having a relaxed configuration with substantially no tendency to self-expand absent an expansive force caused by inflating the balloon;

wherein the balloon in its deflated state defines a series of ridges in a region of the balloon underneath the crimped stent, and defines a first and second balloon shoulder located immediately proximal and distal of the stent and a balloon bed portion defined between the balloon shoulders, wherein the ridges each extend around the entire circumference of the deflated balloon; each ridge having a constant wall thickness with a convex outer surface and a concave inner surface; thereby tending to fictionally retain the stent in an initial longitudinal position while the catheter system is advanced or withdrawn along a vascular path and;

wherein the balloon is adapted to inflate and expand the stent to a larger deployed stent diameter, whereby the balloon assumes substantially the inflated state with said cylindrical working portion above a transition pressure; such that the ridges are substantially not present in the inflated state; whereby the stent delivery system tends to retain the stent in an initial longitudinal position while the catheter system is advanced or withdrawn along a vascular path.

2. The balloon catheter stent deployment system of claim 1, wherein said stent is formed of metal.

3. The balloon catheter stein deployment system of claim 1, wherein the stent has a coating.

4. The balloon catheter stent deployment system of claim 3, wherein the coating is loaded with a therapeutic compound or drug, and is adapted to release it for treatment over time.

5. The balloon catheter stent deployment system of claim 1, the stent further comprising a repeating series of structural elements and flexible links wherein the elements and flexible links is aligned with the series of balloon ridges, to further enhance frictional retention of the stent on the balloon.

6. The balloon catheter stent deployment system of claim 1, wherein individual ridges extend radially outward to varying dimensions.

7. The balloon catheter stent delivery system of claim 1, wherein the stent has a therapeutic drug-release coating.

8. The balloon catheter stent deployment system of claim 3, wherein the coating includes the drug rapamycin.

9. The balloon catheter stent deployment system of claim 3, wherein the coating includes the drugs rapamycin and heparin.

10. The balloon catheter stern deployment system of claim 3, wherein the coating includes one or more of the group of anticoagulants, protein inhibitors, thrombolytics, and anti-proliferitives.

11. The balloon catheter stent deployment system of claim 1, the stent further comprising a repeating series of structural elements and flexible links.

12. The balloon catheter stent deployment system of claim 1, further comprising a hydrophilic coating on at least a portion the stent and balloon.

13. A balloon catheter stent delivery system, comprising:
a balloon catheter with a flexible shaft having proximal and distal ends, a hub affixed to the shaft proximal end having an inflation port, and an inflatable balloon affixed to the shall near the shaft distal end; the shaft defining an inflation lumen providing fluid communication of an inflation fluid between the hub inflation port and the balloon;

wherein the balloon is formed of a substantially inelastic material; such that the balloon is adapted for selective inflation from a deflated state to an inflated state, as well as later deflation; wherein the balloon is initially in a deflated state having a deflated profile shape; wherein the balloon in its inflated state has a cylindrical working portion with an inflated diameter located between a pair of conical portions and a pair of proximal and distal legs affixed to the shaft;

an expandable tubular mesh stent defining a tubular wall thickness, mounted around the balloon and being crimped in an initial state to an initial crimped outer diameter; the stent having a series of structural elements and flexible links;

and wherein the balloon in its initial deflated state defines a series of ridges in a region underneath the crimped stent; wherein the ridges each extend around the entire circumference of the deflated balloon; such that the ridges are substantially not present in the inflated state; each ridge having a constant wall thickness with a convex outer surface and a concave inner surface; and the series of ridges of the balloon in its initial deflated state being arranged to substantially align each one of the series of ridges with one of the series of stent structural elements or flexible links.

14. The balloon catheter of claim 13, wherein the balloon ridges have a shape in cross-section that is arcuate.

15. The balloon catheter of claim 13, wherein the balloon in the deflated shape forms a plurality of folded pleats, wrapped around the shaft; the pleats tending to expand and unfold in the inflated shape.

16. The balloon catheter of claim 13, wherein ridges have a shape in cross-section that is elliptical.

17. The balloon catheter of claim 13, wherein the stent has a therapeutic drug coating.

18. The balloon catheter stent deployment system of claim 1, wherein the stent has an anti-restenosis coating.

* * * * *